United States Patent [19]

Moffett

[11] 4,016,165
[45] Apr. 5, 1977

[54] TRIAZINO BENZODIAZEPINES

[75] Inventor: Robert Bruce Moffett, Kalamazoo, Mich.

[73] Assignee: The Upjohn Company, Kalamazoo, Mich.

[22] Filed: Feb. 9, 1976

[21] Appl. No.: 656,371

[52] U.S. Cl. .......................... 260/248 AS; 424/249
[51] Int. Cl.² ....................................... C07D 253/08
[58] Field of Search .............................. 260/248 AS

[56] References Cited
UNITED STATES PATENTS

| 3,818,003 | 6/1974 | Szmuszkovicz | 260/248 |
| 3,933,816 | 1/1976 | Szmuszkovicz | 260/248 |

Primary Examiner—John M. Ford
Attorney, Agent, or Firm—Hans L. Berneis

[57] ABSTRACT

Compounds of formula IV:

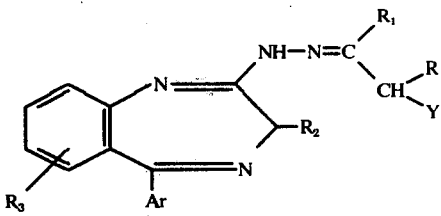

wherein R and $R_1$ are hydrogen or alkyl of 1 to 3 carbon atoms, inclusive; wherein $R_2$ is hydrogen or methyl; wherein $R_3$ is hydrogen, fluoro, chloro, bromo, trifluoromethyl or nitro; and wherein Ar is phenyl, o-chlorophenyl, o-fluorophenyl, 2,6-difluorophenyl or 2-pyridyl, are produced by reacting a hydrazino compound of the formula I

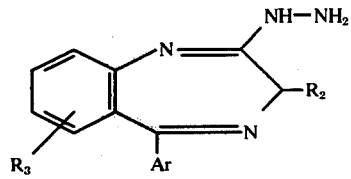

wherein $R_2$, $R_3$, and Ar are defined as above, with a carbonyl reagent of the formula II:

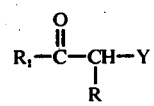

wherein R and $R_1$ are defined as above and Y is chloro, bromo, iodo or

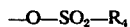

in which $R_4$ is alkyl, defined as above, phenyl, or tolyl, to give the compound III:

III wherein R, $R_1$, $R_2$, $R_3$, Ar, and Y are defined as above and heating compound III, in an inert organic solvent, to give compound IV above.

The compounds of formula IV of this invention and the pharmacologically acceptable acid addition salts thereof are sedatives, tranquilizers and muscle-relaxants and can be used for such purposes in mammals and birds.

11 Claims, No Drawings

TRIAZINO BENZODIAZEPINES

BACKGROUND OF THE INVENTION

FIELD OF THE INVENTION

This invention is concerned with new organic compounds and more particularly with triazinobenzodiazepines and methods for the production thereof.

The new products of this invention and the process of production thereof can be illustratively represented by the following formulae:

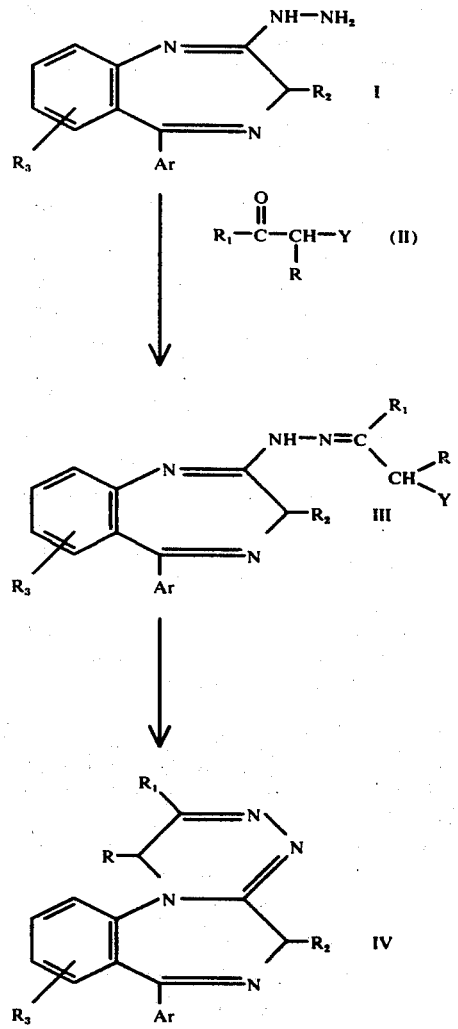

wherein R and $R_1$ are hydrogen or alkyl of 1 to 3 carbon atoms, inclusive; wherein $R_1$ is hydrogen or alkyl as defined above; wherein $R_2$ is hydrogen or methyl; wherein $R_3$ is hydrogen, fluoro, chloro, bromo, trifluoromethyl, or nitro; and wherein Ar is phenyl, o-chlorophenyl, o-fluorophenyl, 2,6-difluorophenyl or 2-pyridyl; and wherein Y is chloro, bromo, iodo, or $$-O-SO_2-R_4$$

in which $R_4$ is alkyl defined as above, phenyl or tolyl.

The invention encompasses besides the compounds of formula IV, the pharmacologically acceptable acid addition salts of these compounds.

The more desirable products of this invention have the formula IVa:

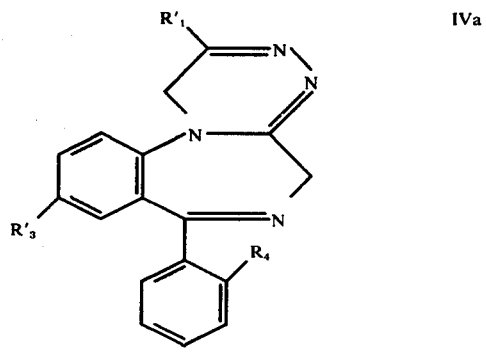

wherein $R'_1$ is hydrogen or alkyl of 1 to 3 carbon atoms, wherein $R'_3$ is hydrogen, fluoro, chloro, bromo, trifluoromethyl, and nitro, and wherein $R_4$ is hydrogen, chloro, or fluoro, and the pharmacologically acceptable acid addition salts thereof.

The most desirable compounds of this invention are of the formula IVb:

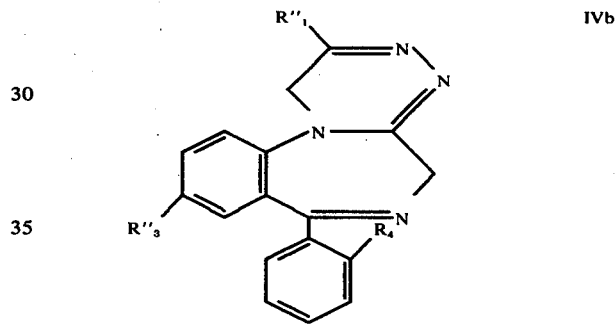

wherein $R''_1$ is hydrogen or methyl; wherein $R_4$ is hydrogen, chloro, or fluoro; and wherein $R''_3$ is chloro, fluoro, and trifluoromethyl, and the pharmacologically acceptable acid addition salts thereof.

The process of the present invention comprises: treating a compound of formula I with a reagent of formula II to give the corresponding 2-(substituted-hydrazino)benzodiazepine III; and heating III to cyclize it to provide the final product IV.

DESCRIPTION OF THE PREFERRED EMBODIMENT

Alkyl groups of 1 to 3 carbon atoms, inclusive, are exemplified by methyl, ethyl, propyl, and isopropyl.

The novel compounds of the formula IV and pharmacologically acceptable addition salts thereof have sedative, hypnotic, anticonvulsant, tranquilizing, and muscle relaxant effects in mammals, including man, and birds. Also as feed additives they increase growth rate and feed efficiency of livestock and poultry.

The pharmacologically acceptable acid addition salts of compounds of formula IV contemplated in this invention, are the hydrochlorides, hydrobromides, hydriodides, sulfated, phosphates, cyclohexanesulfamates, methanesulfonates and the like, prepared by reacting a compound of formula IV with the selected pharmacologically acceptable acid, or obtained directly in the reaction III to IV.

Sedative effects of compounds of formula IV are shown by the following tests in mice:

Chimney test: [Med. Exp. 4, 145 (1961)]: The test determines the ability of mice to back up and out of a vertical glass cylinder within 30 seconds. At the effective dosage, 50% of the mice failed doing it.

Dish test: Mice in Petri dishes (10 cm. diameter, 5 cm. high, partially embedded in wood shavings), climb out in a very short time, when not treated. Mice remaining in the dish for more than 3 minutes indicates tranquilization. $ED_{50}$ equals the dose of test compound at which 50% of the mice remain in the dish.

Pedestal test: The untreated mouse leaves the pedestal in less than a minute to climb back to the floor of the standard mouse box. Tranquilized mice will stay on the pedestal for more than 1 minute.

Nicotine antagonism test: Mice in a group of 6 are injected with the test compound. Thirty minutes later the mice including control (untreated) mice are injected with nicotine salicylate (2 mg./kg.). The control mice show overstimulation, i.e., (1) running convulsions followed by (2) tonic extensor fits; followed by (3) death. The intraperitoneal dosage of the test compound which protects 50% of the mice against (2) and (3) is the $ED_{50}$.

Antagonism to strychnine (as sulphate): The test consists in intraperitoneally administering into groups of 6 mice the test compound, and 30 minutes later 3 mg./kg. strychnine sulfate is also given intraperitioneally. The survivors after 4 hours reflect the activity of the compound as a muscle relaxant and antispasmodic. A dosage of 3 mg./kg. of strychnine sulfate is routinely fatal to all the control mice. A dosage which protects 50% of the mice from death is the $ED_{50}$.

The pharmaceutical forms contemplated by this invention include pharmaceutical compositions suited for oral, parenteral, and rectal use, e.g., tablets, powder packets, cachets, dragees, capsules, solutions, suspensions, sterile injectable forms, suppositories, bougies, and the like. Suitable diluents or carriers such as carbohydrates (lactose), proteins, lipids, calcium phosphate, cornstarch, stearic acid, methylcellulose and the like may be used as carriers or for coating purposes. Oil, e.g., coconut oil, sesame oil, safflower oil, cottonseed oil, peanut oil may be used for preparing solutions or suspensions of the active drug. Sweetening, coloring, and flavoring agents may be added.

For mammals and birds food premixes, with starch, oatmeal, dried fishmeat, fishmeal, flour, and the like can be prepared.

As tranquilizer the compounds of formula IV and the pharmacologically acceptable acid addition salts thereof can be used in dosages of 0.05–2.0 mg./kg. preferably 0.1–2.0 mg./kg. in oral or injectable preparations as described above, to alleviate tension and anxiety in mammals, or birds, such as e.g. occurs when animals are in travel.

Other acid addition salts of the compounds of formula II can be made such as the fluosilicic acid addition salts which are useful mothproofing compounds or the trichloroacetates useful as herbicides against Johnson grass, Bermude grass, yellow foxtail and green foxtail, and quack grass.

The starting compounds of formula I of this invention are synthesized as shown in e.g. In Tetrahedron Letters, 4039, (1970).

The reactants of formula II are to a large extent commercially available, or can be made as shown by Pettison et al., Can. J. Chem. 34, 757 (1956); Gershman et al., J. Org. Chem. 31, 2833 (1966); Malinowski et al., Ukr. Khim Zh 30, 1336 (1964); Crowther et al., J. Chem. Soc. 2818 (1963); Borowitz et al., J. Org. Chem. 34, 2687 (1969); Catch et al., J. Chem. Soc. 278 (1948); Hunig et al., Ann. Chem. 748, 173 (1971).

In carrying out the process of this invention a selected compound I, preferably, but not necessarily dissolved in an inert organic solvent, is treated with reagent II. Inert organic solvents useful in this reaction are tetrahydrofuran, dioxane, glyme, diglyme, benzene, toluene, methylene chloride, chloroform and the like. Temperatures for this reaction are between −20° to 80° C., preferably about room temperature (20° to 25° C.). For benzene temperatures above its melting point of 5.5° C. must be used. The reactant II is used in equimolar to equimolar +50% quantity in relation to the starting benzodiazepine I. After the reaction is terminated the product III is recovered and purified in conventional manner e.g. by evaporation of the mixture, extraction, redissolving and filtering the impure product III, chromatography and crystallization.

Product III is cyclized in a solvent, preferably in toluene, but tetrahydrofuran, glyme, and diglyme can be used, at a temperature between 20° to 200° C. preferably between 25° to 125° C. Toluene is preferred since the product IV formed under reflux conditions (about 111° C.) separates from the mixutre as the acid addition salts and can be recovered by filtration. Compound IV is purified in conventional manner by chromatography and crystallization.

If other solvents are employed for the cyclization, compound IV is obtained by conventional evaporation or extraction procedures or conversion to the free base and purified as above.

Compound IV can also be obtained by increasing the pot temperature of the first step reaction, which will provide directly from compound I compound IV without isolation of compound III.

The following preparation and examples are illustrative of the processes and products of the present invention, but are not to be construed as limiting.

EXAMPLE 1

7-Chloro-2-[(2-chloro-1-methylethylidene)-hydrazino]-5-(o-chlorophenyl)-3H-1,4-benzodiazepine A mixture of 3.19 g. (0.01 mole) of 7-chloro-5-(o-chlorophenyl)-2-hydrazino-3H-1,4-benzodiazepine and 100 ml. of tetrahydrofuran, under nitrogen, was cooled to 0° C. and 1 ml. of chloropropanone was slowly added with stirring. The mixture was allowed to warm to room temperature; after one-half hour all the solid had dissolved. After stirring for a total of 2 hours, thin layer chromatography ($SiO_2$, 20% methanol/benzene) showed essentially one spot. Evaporation at room temperature in vacuo gave a light brown gum which was dissolved in absolute ether and filtered. The solution was concentrated by a stream of $N_2$ on a steam bath to a small volume and pentane was added. After cooling in the refrigerator, the resulting crystals were collected, washed with ether and pentane and dried, yielding 3.82 g. (97%) of 7-chloro-2-[(2-chloro-1-methylethylidene)hydrazinoe]-5-(o-chlorophenyl)-3H-1,4-benzodiazepine.

Anal. calcd. for $C_{18}H_{15}Cl_3N_4$: C, 54.91; H, 3.84; Cl, 27.01; N, 14.23.

Found: C, 54.62; H, 4.13; Cl, 27.35; N, 14.23.

EXAMPLE 2

7-Chloro-1,3-dihydro-5-phenyl-2H-1,4-benzodiazepin-2-one, (2-chloroethylidene)hydrazone A solution of 2.85 g. (0.01 mole) of 7-chloro-2-hydrazino-5-phenyl-3H-1,4-benzodiazepine in 38 ml. of tetrahydrofuran was cooled in a nitrogen atmosphere to −78° by Dry Ice and 0.82 ml. (1.02 g., 0.013 mole) of chloroacetaldehyde as added dropwise with stirring. After 3 hours of −80° and 16 hours at −15° C. no starting material was present as determined by thin layer chromatography. The reaction mixture was evaporated to dryness in vacuo giving a crystalline residue, which was boiled with 800 ml. of eter, and then filtered. The filtrate was concentrated to about 100 ml. at which point a considerable amount of solid precipitated. After cooling in a refrigerator, the solid was collected yielding 1.8 g. of nearly white crystals of melting point 210°–235° C. (with decomposition, and darkening from 150° C. upward). Thin layer chromatography showed essentially one spot, and the infrared, NMR, and mass spectrography also support the structure.

Anal. calcd. for $C_{17}H_{14}Cl_2N_2$: C, 59.14; H, 4.09; N, 16.23; Cl, 20.54.

Found: C, 59.04; H, 4.17; N, 16.14.

EXAMPLE 3

7-Chloro-2-[(2-chloro-1-methylethylidene)-hydrazino]-5-phenyl-3H-1,4-benzodiazepine A solution of 2.85 g. (0.01 mole) of 7-chloro-2-hydrazino-5-phenyl-3H-1,4-benzodiazepine in 75 ml. of tetrahydrofuran, under nitrogen, was cooled to 0° C. and 1 ml. of chloroacetone was added during 10 minutes with stirring. After stirring at 0° C. for 0.5 hours and at room temperature for 2 hours the mixture was evaporated in vacuo at room temperature. The residue was dissolved in 150 ml. of ethyl acetate, filtered hot, concentrated to 50 ml. and cooled giving 2.93 g. (79%) of 7-chloro-2-[(2-chloro-1-methylethylidene)hydrazino]-5-phenyl-3H-1,4-benzodiazepine of melting point 210°–227° C. (decomposition with darkening from 160° C. up).

Anal. calcd. for $C_{18}H_{18}Cl_2N_4$: C, 60.18; H, 4.49; Cl, 19.74; N, 15.60.

Found: C, 59.92; H, 4.53; Cl, 19.39; N, 15.49.

EXAMPLE 4

7-Chloro-2-[(2-chloro-1-methylethylidene)-hydrazino]-5-(2,6-difluorophenyl)-3H-1,4-benzodiazepine In the manner given in Example 1, 7-chloro-2-hydrazino-5-(2,6-difluorophenyl)-3H-1,4-benzodiazepine can be reacted with chloropropanone to give 7-chloro-2-[2-chloro-1-methylethylidene)hydrazino]-5-(2,6-difluorophenyl)-3H:1,4-benzodiazepine.

EXAMPLE 5

7-Bromo-2-[(2-chloro-1-methylethylidene)-hydrazino]-5-(2-pyridyl)-3H-1,4-benzodiazepine In the manner given in Example 1, 7-bromo-2-hydrazino-5-(2-pyridyl)-3H-1,4-benzodiazepine can be reacted with chloropropanone to give 7-bromo-2-[(2-chloro-1-methylethylidene)hydrazino]-5-(2-pyridyl)-3H-1,4-benzodiazepine.

EXAMPLE 6

2-[(2-Chloro-1-methylethylidene)hydrazino]-5-(o-chlorophenyl)-3H-1,4-benzodiazepine In the manner given in Example 1, 2-hydrazino-5-(o-chlorophenyl)-3H-1,4-benzodiazepine can be reacted with chloropropanone to give 2-[(2-chloro-1-methylethylidene)hydrazino]-5-(o-chlorophenyl)-3H-1,4-benzodiazepine.

EXAMPLE 7

7-Chloro-2-[(2-bromoethylidene)hydrazino]-5-phenyl-3H-1,4-benzodiazepine

In the manner given in Example 1, 7-chloro-2-hydrazino-5-phenyl-3H-1,4-benzodiazepine can be reacted with α-bromoacetaldehyde to give 7-chloro-2-[(2-bromoethylidene)hydrazino]-5-phenyl-3H-1,4-benzodiazepine.

EXAMPLE 8

7-Chloro-2-[(2-chloroethylidene)hydrazino]-5-(o-chlorophenyl)-3-H-1,4-benzodiazepine In the manner given in Example 1, 7-chloro-2-hydrazino-5-(o-chlorophenyl)-3H-1,4-benzodiazepine can be reacted with α-chloroacetaldehyde to give 7-chloro-2-[(2-chloroethylidene)hydrazino]-5-(o-chlorophenyl)-3H-1,4-benzodiazepine.

EXAMPLE 9

7-Fluror-2-[(2-chloro-1-methylethylidene)-hydrazino]-5-phenyl-3H-1,4-benzodiazepine In the manner given in Example 1, 7-fluoro-2-hydrazino-5-phenyl-3H-1,4-benzodiazepine can be reacted with chloropropanone to give 7-fluoro-2-[(2-chloro-1-methylethylidene)hydrazino]-5-phenyl-3H-1,4-benzodiazepine.

EXAMPLE 10

7-Nitro-2-[(2-chloro-1-methylethylidene)-hydrazino]-5-phenyl-3H-1,4-benzodiazepine In the manner given in Example 1, 7-nitro-2-hydrazino-5-phenyl-3H-1,4-benzodiazepine can be reacted with chloropropanone to give 7-nitro-2-[(2-chloro-1-methylethylidene)-hydrazino]-5-phenyl-3H-1,4-benzodiazepine.

EXAMPLE 11

7-(Trifluoromethyl)-2-[(2-bromo-1-methylethylidene)hydrazino]-5-phenyl-3H-1,4-benzodiazepine In the manner given in Example 1, 7-(trifluoromethyl) -2-hydrazino-5-phenyl-3H-1,4-benzodiazepine can be reacted with bromopropanone to give 7-(trifluoromethyl)-2-[ (2-bromo-1-methylethylidene)hydrazino]-5-phenyl-3H-1,4-benzodiazepine.

EXAMPLE 12

7-Chloro-2-[(2-hydroxy-1-methylethylidene)-hydrazino] -5-(o-fluorophenyl)-3H-1,4-benzodiazepine, methanesulfonate (ester)

In the manner given in Example 1, 7-chloro-2-hydrazino-5-(o-fluorophenyl-3H-1,4-benzodiazepine can be reacted with 2-oxopropyl methanesulfonate to give 7-chloro-2-[(2-hydroxy-1-methylethylidene)hydrazino]-5-(o-fluorophenyl) -3H-1,4-benzodiazepine, methanesulfonate (ester).

EXAMPLE 13

7-Bromo-2-[(2-hydroxyl-1-methylethylidene)-hydrazino] -5-phenyl-3H-1,4-benzodiazepine, benzenesulfonate (ester)

In the manner given in Example 1, 7-bromo-2-hydrazino-5-phenyl-3H-1,4-benzodiazepine can be reacted with 2-oxopropyl benzenesulfonate to give 7-bromo-2-[(2-hydroxy-1-methylethylidene) hydrazino]-5-phenyl-3H-1,4-benzodiazepine, benzenesulfonate (ester).

EXAMPLE 14

7-Chloro-2-hydroxy-1-ethylethylidene)-hydrazino] -5-phenyl-3H-1,4-benzodiazepine, p-toluenesulfonate (ester)

In the manner given in Example 1, 7-chloro-2-hydrazino-5-phenyl-3H-1,4-benzodiazepine can be reacted with 2-oxobutyl p-tolunesulfonate to give 7-chloro-2-[(2-hydroxy-1-ethylethylidene) hydrazino]-5-phenyl-3H-1,4-benzodiazepine, p-toluenesulfonate (ester).

EXAMPLE 15

7-Chloro-2-[(2-chloro-1-propylethylidene)-hydrazino] -5-phenyl-3H-1,4-benzodiazepine In the manner given in Example 1, 7-chloro-2-hydrazino-5-phenyl-3H-1,4-benzodiazepine can be reacted with 1-chloro-2-pentanone to give 7-chloro-2-[(2-chloro-1-propylethylidene) hydrazino]-5-phenyl-3H-1,4-benzodiazepine.

EXAMPLE 16

7-Chloro-2-[(2-chloro-1-methylpropylidene)-hydrazino] -5-phenyl-3H-1,4-benzodiazepine In the manner given in Example 1, 7-chloro-2-hydrazino-5-phenyl-3H-1,4-benzodiazepine can be reacted with 3-chloro-2-butanone to give 7-chloro-2-[(2-chloro-1-methylpropylidene) hydrazino]-5-phenyl-3H-1,4-benzodiazepine.

EXAMPLE 17

7-Chloro-2-[(2-chloropropylidene)hydrazino]-5-(o-chlorophenyl)-3H-1,4-benzodiazepine In the manner given in Example 1, 2-hydraino-5-(o-chlorophenyl)-3H-1,4-benzodiazepine can be reacted with 2-chloropropional dehyde to give 7-chloro-2-[(2-chloropropylidene) hydrazino]-5-(o-chlorophenyl)-3H-1,4-benzodiazepine.

EXAMPLE 18

7-Chloro-2-[(2-chloro-1-methylethylidene)-hydrazino] -5-phenyl-3H-1,4-benzodiazepine In the manner given in Example 1, 7-chloro-2-hydrazino -5-phenyl-3H-1,4-benzodiazepine can be reacted with 3-chloro-4-penten-2-one to give 7-chloro-2-[(2-chloro-2 -vinyl-1-methylethylidene)hydrazino]-5-phenyl-3H-1,4-benzodiazepine.

In the manner given in the preceding examples, other compounds of formula III can be prepared. representative compounds, thus prepared, include:

7-nitro-2-[(2-chloro-1-propylethylidene)hydrazino]-5-(o-chlorophenyl) -3H-1,4-benzodiazepine;
7-fluoro-2-[(2-chloro-1-methylethylidene)hydrazino]-5-(o-chlorophenyl) -3H-1,4-benzodiazepine;
6-fluoro-2-[(2-chloro-1-methylethylidene)hydrazino]-5-(o-fluorophenyl) -3H-1,4-benzodiazepine;
9-chloro-2-[(2-chloro-1-methylethylidene)hydrazino]-5 -(o-chlorophenyl)-3H-1,4-benzodiazepine;
8-trifluoromethyl-2-[(2-chloro-1-methylethylidene)-hydrazino] -5-phenyl-3H-1,4-benzodiazepine;
6-bromo-2-[2-chloro-1-ethylethylidene)hydrazino]-5-(o-fluorophenyl) -3H-1,4-benzodiazepine;
8-nitro-2-[2-chloro-1-propylethylidene)hydrazino]-5-(O-chlorophenyl) -3H-1,4-benzodiazepine;
2-[2-chloro-1-methylpropylidene)hydrazino]-5-(2,6-difluorophenyl) -3H-1,4-benzodiazepine;
2-[2-chloro-1-ethylpropylidene)hydrazino]-5-(2-pyridyl)-3H -1,4-benzodiazepine;
6-fluoro-2-[2-chloro-1-ethylpropylidene)hydrazino]-5-(2-pyridyl)-3H-1,4-benzodiazepine;
and the like.

EXAMPLE 19

9-Chloro-7-(o-chlorophenyl)-1,5-dihydro-2-methyl -as-triazino[4,3-a][1,4]benzodiazepine hydrochloride A solution of 3.15 g. (0.008 mole) of 7-chloro-2-[(2-chloro-1-methylethylidene) hydrazino]-5-(o-chlorophenyl)-3H -1,4-benzodiazepine in 50 ml. of toluene, under nitrogen was stirred under reflux for 2.5 hours and allowed to stand for 3 days. The resulting solid was collected giving 1.78 g. of brown crystals. These crystals were dissolved in 60 ml. of methanol, treated at the boiling point with decolorizing charcoal (Darco G-60), filtered, and the mixture was concentrated to 15 ml. Diluton at boiling point to 50 ml. with absolute ether and cooling yielded 1.22 g. (38.8% of 9-chloro-7-(o-chlorophenyl)-1,5 -dihydro-2-methyl-as-triazino[4,3-a][1,4]benzodiazepine hydrochloride of melting point 250—260° C. with decomposition from 225° C. up.

Anal. calcd. for $C_{18}H_{14}Cl_2N_4 \cdot HCl$: C, 54.91; H, 3.84; Cl, 27.01; N, 14.23. Found: C, 54.75; H, 4.09; cl, 26.94; N, 14.33.

EXAMPLE 20

9-Chloro-1,5-dihydro-2-methyl-7-phenyl-as-triazino [4,3-a][1,4]benzodiazepine and its hydrochloride A suspension of 1.8 g. (0.005 mole) of 7-chloro-2-[(2-chloro-1-methylethylidene) hydrazino]-5-phenyl-3H-1,4 -benzodiazepine in 20 ml. of diethyleneglycol dimethylether under nitrogen was stirred under reflux (bath 170° C.) for 1 hour. The mixture became very dark and the solid was never all in solution but seemed to change. After cooling the solid was collected, washed with diglyme and dried, weight 0.75 g.

This hydrochloride salt was mixed with dilute aqueous sodium hydroxide and extracted with chloroform. The chloroform solution was dried over anhydrous magnesium sulfate, filtered and evaporated (56°/0.1 mm) giving 0.6 g. of brown crystalline solid. This was dissolved in chloroform, treated with Darco G-60, filtered, concentrated and diluted with absolute ether. After standing 3 hours the product was collected, washed with ether and dried giving 0.35 g. (22%) of 9-chloro-1,5-dihydro -2-methyl-7-phenyl-as-triazino[4,3-a][1,4]benzodiazepine of melting point 170°–197° C. (decomp. with darkening from 150° C. up).

Anal. calcd. for $C_{18}H_{15}ClN_4 \cdot 0.0471\ CHCl_3$: C, 66.01; H, 4.62; N, 17.06. Found: C, 65.94; H, 4.67; N, 17.41.

9-Chloro-1,5-dihydro-2-methyl-7-phenyl-as-triazino-[4,3-a] [1,4]benzodiazepine hydrochloride — A solution of 0.28 g. of the above free base, 9-chloro-1,5-dihydro-2 -methyl-7-phenyl-as-triazino[4,3-a] [1,4]benzodiazepine in 10 ml. of 2-propanol was acidified with 0.2 ml. of 4.4 N ethanolic hydrochloric acid. The resulting crystals were collected, washed with 2-propanol and ether and dried giving 0.24 g. (77%) of 9-chloro-1,5-dihydro -2-methyl-7-phenyl-as-triazino[4,3-a] [1,4]benzodiazepine hydrochloride of melting point 225°–235° C. (decomp. with darkening from 200° C. up). Ir was identical with the hydrochloride prepared directly below:

A solution of 0.72 g. (0.002 mole) of 7-chloro-2 -[(2-chloro-1-methylethylidene)hydrazino]-5-phenyl-3H -1,4-benzodiazepine and 1-chloro-2-propanone in 25 ml. of toluene (all in solution at 90° C.), under nitrogen, was stirred under reflux for 4 hours. After standing overnight the resulting crystals were collected, washed with toluene and ether and dried to give 0.32 g. of brown solid. This was dissolved in 20 ml. of methanol, treated at the boiling point with activated charcoal [Darco G-60], filtered, concentrated, by a stream of nitrogen on a steam bath to about 5 ml. and diluted with 2-propanol. Concentration was continued until crystallization started. After cooling, the product was collected, washed with 2-propanol and ether and dried yielding 0.2 g. (28%) of pale blue-green crysals. Ir was identical with the above hydrochloride and had a melting point 235°–245° C. (decomp. with darkening from 213° C. up).

Anal. calcd. for $C_{18}H_{18}Cl_2N_4$: C, 60.18; H, 4.49; cl, 1974; N, 15.60. Found: C, 60.08; H, 4.53; Cl, 1958; N, 15.82.

EXAMPLE 21

9-Chloro-1,5-dihydro-2-methyl-7-(2,6-difluorophenyl) -as-triazino[4,3-a] [1,4]benzodiazepine In the manner given in Example 19, 7-chloro-1-[(2-chloro -1-methylethylidene)hydrazino]-5-(2,6-difluorophenyl) -3H-1,4-benzodiazepine in xylene can be heated to reflux to give 9-chloro-1,5-dihydro-2-methyl-7-(2,6-difluorophenyl) -as-triazino[4,3-a] [1,4]benzodiazepine as the hydrochloride.

EXAMPLE 22

9-Bromo-1,5-dihydro-2-methyl-7-(2-pyridyl)-as-triazino [4,3-a] [1,4]benzodiazepine In the manner given in Example 20, 7-bromo-2-[(2-chloro -1-methylethylidene)hydrazino]-5-(2-pyridyl)- 3H-1,4 -benzodiazepine in diglyme can be heated to reflux to give 9-bromo-1,5-dihydro-2-methyl-7-(2-pyridyl)-as-triazino [4,3-a] [1,4]benzodiazepine.

EXAMPLE 23

1,5-Dihydro-2-methyl-7-(o-chlorophenyl)-as -triazino[4,3-a] [1,4]benzodiazepine hydrochloride In the manner given in Example 19, 2-[(2-chloro-1-methylethylidene) hydrazino]-5-(o-chlorophenyl)-3H-1,4-benzodiazepine in toluene can be heated to reflux to give 1,5-dihydro-2-methyl-7-(o-chlorophenyl)-as-triazineo-[4,3-a] [1,4]benzodiazepine as the hydrochloride.

EXAMPLE 24

9-Chloro-1,5-dihydro-7-phenyl-as-triazino-[4,3-a] [1,4]benzodiazepine

In the manner given in Example 19, 7-chloro-2-[(2-bromoethylidene) hydrazino]-5-phenyl-3H-1,4-benzodiazepine in xylene can be heated to reflux to give 9-chloro-1,5-dihydro -7-phenyl-as-triazino[4,3-a] [1,4]benzodiazepine as the hydrobromide.

EXAMPLE 25

9-Chloro-1,5-dihydro-7-(o-chlorophenyl)-as-triazino [4,3-a] [1,4]benzodiazepine and its hydrochloride In the manner given in Example 19, 7-chloro-2-[(2-chloroethylidene) hydrazino]-5-(o-chlorophenyl)-3H-1,4-benzodiazepine in toluene can be heated to reflux to give 9-chloro-1,5-dihydro-7-(o-chlorophenyl)-as-triazino-[4,3-a] [1,4]benzodiazepine as the hydrochloride.

The free base can be obtained by reacting the 9-chloro -1,5-dihydro-7-(o-chlorophenyl)-as-triazino[4,3-al]-[1,4] benzodiazepine hydrochloride with e.g. sodium bicarbonate in aqueous tetrahydrofuran and extracting the free base with chloroform.

EXAMPLE 26

9-Fluoro-1,5-dihydro-2-methyl-7-phenyl-as -triazino[4,3-a] [1,4]benzodiazepine

In the manner given in Example 19, 7-fluoro-2-[(2-chloro -1-methylethylidene)hydrazino]-5-phenyl-3H-1,4-benzodiazepine in toluene can be heated to reflux to give 9-fluoro-1,5-dihydro-2-methyl-7-phenyl-as-triazino-[4,3-a] [1,4]benzodiazepine as the hydrochloride.

EXAMPLE 27

9-Nitro-1,5-dihydro-2-methyl-7-phenyl-as-triazino [4,3-a] [1,4]benzodiazepine

In the manner given in Example 20, 7-nitro-2-[(2-chloro -1-methylethylidene)hydrazino]-5-phenyl-3H-1,4-benzodiazepine in glyme can be heated to reflux to give 9-nitro-1,5-dihydro-2-methyl-7-phenyl-as-triazino[4,3-a]-[1,4] benzodiazepine.

EXAMPLE 28

9-(trifluoromethyl)-1,5-dihydro-2-methyl-7-phenyl -as-triazino[4,3-a] [1,4]benzodiazepine In the manner given in Example 19, 7-(trifluoromethyl) -2-[(2-bromo-1-methylethylidene)hydrazino]-5-phenyl -3H-1,4-benzodiazepin in xylene can be heated to give 9-(trifluouromethyl)-1,5-dihydro-2- methyl-7-phenyl -as-triazino[4,3-a] [1,4]benzodiazepine as the hydrobromide.

EXAMPLE 29

9-Chloro-1,5-dihydro-2-methyl-7-(o-fluorophenyl)-as-triazino[4,3-a] [1,4]benzodiazepine and its methanesulfonate salt In the manner given in Example 19, 7-chloro-2-[(2-hydroxy -2-methylethylidene)hydrazino]-5-(o-fluorophenyl) -3H-1,4-benzodiazepine, methanesulfonate (ester) in toluene can be heated to reflux to give 9-chloro-1,5-dihydro -2-methyl-7-(o-fluorophenyl)-as-triazino[4,3-a]-[1,4] benzodiazepine as the methanesulfonate salt. The methanesulfonate can be mixed with an equimolecular amount of sodium hydroxide in water to give the free base, 9-chloro-1,5-dihydro-2-methyl-7-(o-fluorophenyl)-as -triazino[4,3-a] [1,4]benzodiazepine.

EXAMPLE 30

9-Bromo-1,5-dihydro-2-methyl-7-phenyl-as-triazino [4,3-a] [1,4]benzodiazepine benzenesulfonate salt In the manner given in Example 19, 7-bromo-2-[(2-hydroxy -1-methylethylidene)hydrazino]-5-phenyl-3H-1,4-benzodiazepine benzenesulfonate (ester) in xylene can be heated to give 9-bromo-1,5-dihydro-2-methyl-7-phenyl-as -triazino[4,3-a] [1,4]benzodiazepine as the benzenesulfonate salt.

EXAMPLE 31

9-Chloro-1,5-dihydro-2-ethyl-7-phenyl-as-triazino [4,3-a] [1,4]benzodiazepine p-toluenesulfonate salt In the manner given in Example 19, 7-chloro-2-[(2-hydroxy -1-ethylethylidene)hydrubi]-5-phenyl-3H-1,4-benzodiazepine, p-toluenesulfonate (ester) in diglyme can be heated to reflux to give 9-chloro-1,5-dihydro-2-ethyl -7-phenyl-as-triaino[4,3-a] [1,4]benzodiazepine as the p-toluenesulfonate salt.

EXAMPLE 32

9-Chloro-1,5-dihydro-2-propyl-7-phenyl-as-triazino [4,3-a] [1,4]benzodiazepine

In the manner given in Example 20, 7-chloro-2-[(2-chloro -1-propylethylidene(hydrazino]-5-phenyl-3H-1,4-benzodiazepine in diglyme can be heated to reflux to give 9-chloro-1,5-dihydro-2-propyl-7-phenyl-as-triazino[4,3-a] [1,4]benzodiazepine as the hydrochloride.

EXAMPLE 33

9-Chloro-1,5-dihydro-1,2-dimethyl-7-phenyl-as -triazino[4,3-a] [1,4]benzodiazepine hydrochloride In the manner given in Example 19, 7-chloro-2-[(2-chloro -1-methylpropylidene)hydrazino]-5-phenyl-3H-1,4-benzodiazepine in toluene can be heated to give 9-chloro-1,5 -dihydro-1,2-dimethyl-7-phenyl-as-triazino[4,3-a] [1,4]-benzodiazepine as the hydrochloride.

EXAMPLE 34

9-Chloro-1,5-dihydro-1-methyl-7-(o-chlorophenyl) -as-triazino[4,3-a] [1,4]benzodiazepine hydrochloride In the manner given in Example 20, 7-chloro-2-[(2-chloropropylidene) hydrazino]-5-(o-chlorophenyl9-3H-1,4-benzodiazepine can be heated in diglyme to give 9-chloro-1,5 -dihydro-1-methyl-7-(o-chlorophenyl)-as-triazino[4,3-a]-[1,4] benzodiazepine hydrochloride.

In the manner given in the preceding examples, other compounds of formula IV can be synthesized. Representative compounds, thus prepared, include:

9-nitro-1,5-dihydro-1-propyl-7-(o-chlorophenyl)-as-triazino [4,3-a] [1,4]benzodiazepine;
9-fluoro-1-methyl-7-(o-chlorophenyl)-as-triazino[4,3-a]-[1,4] benzodiazepine;
8-fluoro-1-methyl-7-(o-fluorophenyl)-as-triazino[4,3-a]-[1,4] benzodiazepine;
11-chloro-1-methyl-7-(o-chlorophenyl)-as-triazino[4,3-a]-[1,4] benzodiazepine;
10-trifluoromethyl-1-methyl-7-phenyl-as-triazino[4,3-a]-[1,4] benzodiazepine;
8-bromo-1-ethyl-7-(o-fluorophenyl)-as-triazino[4,3-a]-[1,4] benzodiazepine;
10-nitro-1-propyl-7-(o-chlorophenyl)-as-triazino[4,3-a]-[1,4] benzodiazepine;
1,2-dimethyl-7-(2,6-difluorophenyl)-as-triazino[4,3-a]-[1,4] benzodiazepine;
1-methyl-2-ethyl-7-(2-pyridyl)-as-triazino[4,3-a] [1,4]-benxodiazepine;
6-fluoro-1-methyl-2-ethyl-7-(2-pyridyl-as-triazino-[4,3-a] [1,4]benzodiazepine;
and the like.

EXAMPLE 35

9-Chloro-1,5-dihydro-7-phenyl-as-triazino-[4,3-a] [1,4]benzodiazepine (A). 7-Chloro-1,3-dihydro-1-(2,2-dimethoxyethyl)-5-phenyl -2H-1,4-benzodiazepine-2-one To a solution of 27.1 g. (0.1 mole) of 7-chloro-1,3 -dihydro-5-phenyl-2H-1,4-benzodiazepine-2-one in 300 ml. of dry dimethylformamide was added 4.6 g. (0.11 mole) of 57% sodium hydride in mineral oil, under nitrogen and with continuous stirring. After stirring one hour at room temperature, 25.4 g. (0.15 mol) of redistilled bromoacetaldehyde dimethylacetal in 10 ml. of dimethylformamide was added and the reaction mixture is kept at 100° C. with stirring during 16 hours. The mixture was then concentrated in vacuo to one-half the volume, well shaken with ice water and extracted with methylene chloride. The extract was washed with water, dried over $Na_2SO_4$ and evaporated at 25° C. and 0.2 mm.Hg pressure giving a brown oil which was crystallized from 2-propanol yielding 26.2 g. (73% of light brown crystals m.p. 115–117° C. A sample chromatographed on silica gel, eluted with 2% methanol-98% chloroform, evaporated in vacuo, and crystallized from 2-propanol gave 7-chloro -1,3-dihydro-1-(2,2-dimethoxyethyl)-5-phenyl-2H-1,4 -benzodiazepine-2-one of melting point 117° to 119° C.

Anal. calcd. for $C_{19}H_{19}ClN_2O_3$: C, 63.60; H, 5.34; Cl, 9.88; N, 7.80. Found: C, 63.59; H, 5.39; (1, 9.86; N, 7.65.

(B.) 7-Chloro-1,3-dihydro-1-(2,2-dimethoxyethyl)-5-phenyl -2H-1,4-benzodiazepine-2-thione A solution of 7-chloro-1,3-dihydro-1-(2,2-dimethoxyethyl) -5-phenyl-2H-1,4-benzodiazepine-2-one in pyridine can be treated with phosphorus pentasulfide to yield the thione which can be purified by crystallization or chromatography and used in the next step.

Alternatively the enol alkyl ether of 7-chloro-1,2-dihydro -1-(2,2-dimethoxyethyl)-5-phenyl-2H-1,4- benzodiazepine -2-one can be produced by alkylation e.g. with trialkyloxy tetrafluoroborate, methanesulfonyl fluoride, diazomethane, diazoethane or the like.

(C.) (7-Chloro-1,3-dihydro-1-(2,2-dimethoxyethyl)-5-phenyl-2H-1,4-benzodiazepinyl)hydrazine Either the thione or the enol ether form B above can be treated with excess hydrazine in ethanol at 0° to 80° to give (7-chloro-1,3-dihydro-1-(2,2-dimethoxyethyl)-5-phenyl-2H-1,4-benzodiazepinyl)hydrazine.

(D.) 9-Chloro-7-phenyl-1,5-dihydro-as-triazino-[4,3-a] [1,4]benzodiazepine

A solution of (7-chloro-1,3-dihydro-1-(2,2-dimethoxyethyl) -5-phenyl-2h-1,4-benzodiazepinyl)-hydrazine in 95% sulfuric acid can be stirred for 2 hours at room temperature, poured on ice, and neutralized with dilute sodium hydroxide solution. The product, 9-chloro -7-phenyl-1,5-dihydro-as-triazino[4,3-a] [1,4]-benzodiazepine, can be recovered by extraction, evaporation and chromatography.

The pharmacologically acceptable acid additon salts of compounds of formula IV can be prepared and isolated by conventional processes, such as reacting a compound of formula IV with a selected pharmacologically acceptable acid. Such acid include hydrochloric, hydrobromic, phosphoric, sulfuric, acetic, tartaric, lactic, citric, malic, maleic, methanesulfonic, benzenesulfonic, cyclohexanesulfamic acids, toluenesulfonic, and the like. The reaction is conveniently performed in an organic solvent, e.g. ether, dioxane, tetrahydrofuran, ethanol, methanol, or ethyl acetate; the salts can be recovered by crystallization, precipitation or evaporating the solvent. These salts are useful in the same manner as the free base.

I claim:

1. A compound of the formula IV

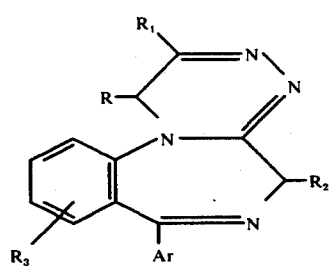

wherein R is hydrogen or alkyl of 1 to 3 carbon atoms, inclusive; wherein $R_1$ is hydrogen or alkyl as defined above; wherein $R_2$ is hydrogen or methyl; wherein $R_3$ is hydrogen, fluoro, chloro, bromo, trifluoromethyl, or nitro; and wherein A is phenyl, o-chlorophenyl, o-fluorophenyl, 2,6-difluorophenyl, or 2-pyridyl, and the pharmacologically acceptable acid addition salts thereof.

2. A compound according to claim 1 of the formula IVa:

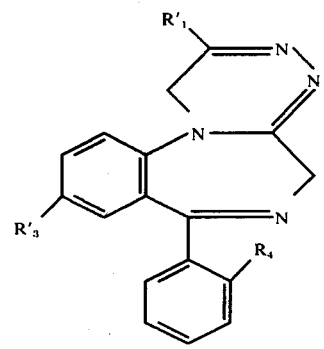

wherein $R_1$ is hydrogen or alkyl of 1 to 3 carbon atoms; wherein $R_3$ is hydrogen, fluoro, chloro, bromo, trifluoromethyl, and nitro, and wherein $R_4$ is hydrogen, chloro, or fluoro, and the pharmacologically acceptable acid addition salts thereof.

3. A compound according to claim 1 of the formula IVb:

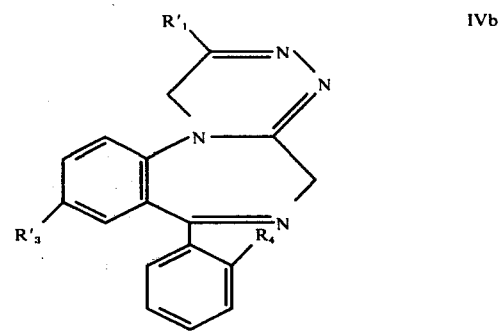

wherein $R'_1$ is hydrogen or methyl; wherein $R_4$ is hydrogen, chloro, or fluoro; wherein $R'_3$ is chloro, fluoro, and trifluoromethyl; and the pharmacologically acceptably acid addition salts thereof.

4. A compound according to claim 3, wherein $R'_1$ is methyl, $R_4$ is hydrogen, $R'_3$ is chloro, and the compound is therefore 9-chloro-1,5-dihydro-2-methyl-7-phenyl -as-triazino[4,3-a] [1,4]benzodiazepine.

5. A compound according to claim 3, wherein $R'_1$ is methyl, $R'_3$ and $R_4$ are chloro; and the compound is therefore 9-chloro-7-(o-chlorophenyl)-1,5-dihydro-2-methyl -as-triazino[4,3-a] [1,4]benzodiazepine.

6. A compound according to claim 1, wherein R and $R_2$ are hydrogen, $R_1$ is methyl, Ar is 2,6-difluorophenyl, $R_3$ is 9-chloro and the compound is therefore 9-chloro-1,5 -dihydro-2-methyl-7-(2,6-difluorophenyl)-as-triazino-[4,3-a] [1,4]benzoodiazepine.

7. A compound according to claim 1, wherein R and $R_2$ are hydrogen, $R_1$ is methyl, $R_3$ is 9-bromo, Ar is 2-pyridyl and the compound if therefore 9-bromo-1,5-dihydro -2-methyl-7-(2-pyridyl)-as-triazino[4,3-a] [1,4]-benzodiazepine.

8. A compound according to claim 3, wherein $R'_1$ is methyl, $R_4$ is chloro or hydrogen, $R'_3$ is hydrogen and the compound is therefore 1,5-dihydro-2-methyl-7-(o-chlorophenyl) -as-triazino[4,3-a] [1,4]benzodiazepine.

9. A compound according to claim 3 as hydrochloride, wherein $R'_1$ is methyl, $R'_3$ is hydrogen, $R_4$ is chloro, and the compound is therefore 1,5-dihydro-2-methyl-7-(o-chlorophenyl) -as-triazino[4,3-a] [1,4]benzodiazepine hydrochloride.

10. A compound according to calim 3, wherein $R'_1$ is hydrogen, $R'_3$ and $R_4$ are chloro and the compound is therefore 9-chloro-1,5-dihydro-7-(o-chlorophenyl)-as-triazino [4,3-a] [1,4]benzodiazepine.

11. A compound according to claim 1, wherein $R_1$ is methyl, R and $R_2$ are hydrogen, $R_3$ is 9-chloro; Ar is o-fluorophenyl and the compound is therefore 9-chloro-1,5 -dihydro-2-methyl-7-(o-fluorophenyl)-as-triazino-[4,3-a] [1,4]benzodiazepine.

* * * * *

UNITED STATES PATENT AND TRADEMARK OFFICE
CERTIFICATE OF CORRECTION

PATENT NO. : 4,016,165
DATED : April 5, 1977
INVENTOR(S) : Robert Bruce Moffett

It is certified that error appears in the above—identified patent and that said Letters Patent are hereby corrected as shown below:

Column 13, line 63: "wherein A" should read -- wherein Ar --
Column 14, line 49: "benzoodiazepine" should read -- benzodiazepine --
          line 52: "compound if" should read -- compound is --
          line 62: "to calim 3" should read -- to claim 3 --

Signed and Sealed this

Twenty-sixth Day of June 1979

[SEAL]

Attest:

RUTH C. MASON
Attesting Officer

DONALD W. BANNER
Commissioner of Patents and Trademarks